United States Patent
Xu

(10) Patent No.: US 12,398,196 B2
(45) Date of Patent: *Aug. 26, 2025

(54) FUSED POLYPEPTIDE WITH MULTIFUNCTIONAL ACTIVITIES AND USE THEREOF

(71) Applicant: NANJING ANJI BIOLOGICAL TECHNOLOGY CO., LTD., Nanjing (CN)

(72) Inventor: Hanmei Xu, Nanjing (CN)

(73) Assignee: NANJING ANJI BIOLOGICAL TECHNOLOGY CO., LTD., Nanjing (CN)

( * ) Notice: Subject to any disclaimer, the term of this patent is extended or adjusted under 35 U.S.C. 154(b) by 723 days.

This patent is subject to a terminal disclaimer.

(21) Appl. No.: 17/635,962

(22) PCT Filed: Oct. 26, 2020

(86) PCT No.: PCT/CN2020/123553
§ 371 (c)(1),
(2) Date: Feb. 16, 2022

(87) PCT Pub. No.: WO2021/037291
PCT Pub. Date: Mar. 4, 2021

(65) Prior Publication Data
US 2022/0332796 A1  Oct. 20, 2022

(30) Foreign Application Priority Data
Aug. 27, 2019  (CN) .......................... 201910796360.X

(51) Int. Cl.
| | | |
|---|---|---|
| *A61K 38/00* | (2006.01) | |
| *A61P 1/16* | (2006.01) | |
| *A61P 9/00* | (2006.01) | |
| *A61P 11/00* | (2006.01) | |
| *A61P 13/12* | (2006.01) | |
| *A61P 17/00* | (2006.01) | |
| *C07K 14/00* | (2006.01) | |
| *C07K 14/81* | (2006.01) | |

(52) U.S. Cl.
CPC ............ *C07K 14/8146* (2013.01); *A61P 1/16* (2018.01); *A61P 9/00* (2018.01); *A61P 11/00* (2018.01); *A61P 13/12* (2018.01); *A61P 17/00* (2018.01); *A61K 38/00* (2013.01); *C07K 2319/00* (2013.01)

(58) Field of Classification Search
CPC ........ A61K 38/00; A61K 38/55; C07K 14/00; C07K 14/8146; C07K 2319/00; C07K 2319/33; A61P 1/16; A61P 11/00; A61P 13/12; A61P 17/00; A61P 9/00
See application file for complete search history.

(56) References Cited

U.S. PATENT DOCUMENTS

2019/0031717 A1* 1/2019 Xu ..................... C07K 14/8146

FOREIGN PATENT DOCUMENTS

| | | |
|---|---|---|
| CN | 101143894 A | 3/2008 |
| CN | 104045718 A | 9/2014 |
| CN | 105713095 A | 6/2016 |
| CN | 109879969 A | 6/2019 |
| CN | 110372800 A | 10/2019 |
| WO | 2015095628 A1 | 6/2015 |
| WO | WO-2017157205 A1 * | 9/2017 ............. A61K 38/16 |

OTHER PUBLICATIONS

Ye et al., "Peptide mediated therapy in fibrosis: Mechanisms, advances and prospects," Biomedicine & Pharmacotherapy, 2023, 157: 1-21. (Year: 2023).*

* cited by examiner

*Primary Examiner* — Julie Ha

(57) ABSTRACT

The present disclosure discloses use of a fused polypeptide with multifunctional activities. In the fused polypeptide with multifunctional activities, the polypeptide contains the following domains: Pro-Arg-Cys-X-Y-Gly-Glu, where X is Trp or Tyr, and Y is Arg or Cys; and Gly-Gly-Gly-Gly-Ile-Val-Arg-Arg-Ala-Asp-Arg-Ala-Ala-Val-Pro-Gly-Gly-Gly-Gly-Arg-Gly-Asp; or a sequence of any amino acid mutated in the foregoing domains. The fused polypeptide can be used for treating various fibrosis diseases and symptoms, including pulmonary fibrosis, hepatic fibrosis, skin fibrosis, renal fibrosis, myocardial fibrosis, and lung tissue lesions.

7 Claims, 5 Drawing Sheets

Specification includes a Sequence Listing.

FUSED POLYPEPTIDE WITH MULTIFUNCTIONAL ACTIVITIES AND USE THEREOF

INCORPORATION BY REFERENCE

The Sequence Listing created on Apr. 11, 2022 with a file size of 3.00 KB, and filed herewith in ASCII text file format as the file entitled "Sequence_Listing-G204RAYT0003US.TXT," is hereby incorporated by reference in its entirety.

TECHNICAL FIELD

The present disclosure relates to the field of biopharmaceuticals, and in particular, to a fused polypeptide for preventing or treating various fibrosis diseases and symptoms, and therapeutic use includes anti-pulmonary fibrosis, anti-hepatic fibrosis, anti-skin fibrosis, anti-renal fibrosis, and anti-myocardial fibrosis.

BACKGROUND

Tissue fibrosis is a disease in which parenchymal cells of organs and tissues decrease and fibrillar connective tissues increase. Continuous progression of the disease may lead to structural damage and hypofunction of organs, and eventually failure, which seriously threatens health of patients. Worldwide, fibrosis of tissues and organs is the main cause of disability and death in many diseases.

In the process of tissue fibrosis, fibroblasts and myofibroblasts are key effector cells of tissue fibrosis. These effector cells can release a large number of collagen components, such as type I and type III collagen, which constitute ECM. A variety of cytokines are also involved in the process of fibrosis, and the most critical one is transforming growth factor-β (TGF-β). TGF-β is a multifunctional cell growth factor that regulates cell proliferation and differentiation, and can directly stimulate the activation of in situ fibroblasts or stimulate the proliferation of a large number of myofibroblasts and the excessive synthesis of ECM through endothelial-mesenchymal transition (EnMT) and epithelial-mesenchymal transition (EMT) processes. When TGF-β is continuously activated due to damage, MAPK, EGF, and Wnt/β-catenin signals are cross-activated, leading to the progression of fibrosis. In addition to TGF-β, the regulation over a platelet-derived growth factor (PDGF), a basic fibroblast growth factor (bFGF), a connective tissue growth factor (CTGF), an insulin-like growth factor (IGF), angiogenesis-related cytokines, integrin, matrix metalloproteinase (MMP) and an inhibitor (TIMP) thereof, renin angiotensin-related protein, natriuretic peptide, and the like also affect occurrence of fibrosis.

1. Pulmonary Fibrosis

Pulmonary fibrosis (PF) is a serious pulmonary interstitial disease caused by many factors, and features the formation of pulmonary fibroblast foci and excessive accumulation of ECM. In view of similar pathological responses and disease characteristics of lung tissues after injury, pulmonary fibrosis is clinically commonly referred to as interstitial lung disease (ILD). Diffuse parenchymal lung disease, alveolar inflammation and interstitial fibrosis are basic pathological lesions of the ILD. Some disease causes are clear, while some disease causes are unknown. If the disease causes are unclear, the disease is referred to as idiopathic pulmonary fibrosis (IPF). Idiopathic pulmonary fibrosis has the highest incidence among pulmonary fibrosis, mostly in elderly men, with a median survival time of 3 years, and is the focus of current research.

Pulmonary fibrosis is a process of excessive repair of lung tissue. Wilson pointed out that when a problem occurs to any one or more links in an "injury-inflammation-repair" chain, the occurrence of fibrosis is caused. At present, the occurrence of pulmonary fibrosis may be attributed to the following three stages: (1) Injury stage: Alveolar epithelial cells are damaged by the stimulation of gas, dust, infection (bacteria or virus), drugs, radiation damage and other factors; (2) Effect stage: Injury promotes the apoptosis of alveolar epithelial cells and leads to oxidative stress response. Inflammatory cells (macrophages, T/B lymphocytes, neutrophils, and the like) recruited at an injury site and a large number of secreted transforming growth factor-β (TGF-β) stimulate the proliferation and differentiation of fibroblasts and promote the formation of lung fibroblast foci; (3) Fibrosis stage: The formation of fibroblast foci and excessive secretion of the ECM lead to the gradual replacement of parenchymal cells of lung tissue by interstitial cells, so that lung tissues lose elasticity and the hardness increases, and finally physiological functions of lung tissues are lost, resulting in that a patient dies due to respiratory failure caused by fibrosis.

A plurality of kinds of cells, such as pulmonary epithelial cells, endothelial cells, pulmonary inflammatory cells (mainly macrophages), and pulmonary interstitial cells (fibroblasts and myofibroblasts), are involved in the occurrence of fibrosis, and the pulmonary interstitial cells are key effector cells for the occurrence of pulmonary fibrosis. In addition, cytokines secreted by cells, such as transforming growth factor-β (TGF-β), a platelet-derived growth factor (PDGF), a basic fibroblast growth factor (bFGF), a connective tissue growth factor (CTGF), an insulin-like growth factor (IGF), a vascular endothelial growth factor (VEGF), integrin, matrix metalloproteinase (MMP), and an inhibitor (TIMP) thereof, also have a profound impact on the occurrence of pulmonary fibrosis.

The most critical cytokine is TGF-β, which is a multifunctional cell growth factor that can regulate cell proliferation and differentiation. The proliferation of a large number of myofibroblasts and the excessive accumulation of the ECM can be stimulated by directly stimulating the activation of in situ fibroblasts or through endothelial-mesenchymal transition (EnMT) and epithelial-mesenchymal transition (EMT) processes. When TGF-β is continuously activated due to damage, MAPK, EGF, and Wnt/β-catenin signals are cross-activated, leading to the progression of fibrosis. The PDGF, the bFGF, and the VEGF as growth factors can promote the proliferation and differentiation of lung fibroblasts, and affect the progression of pulmonary fibrosis. The MMP/TIMP is a main regulator of the ECM, and the contents of the two play a key role in the balance of the ECM. These cytokines have a more or less influence on the proliferation and activation of lung fibroblasts and the formation of collagen, and therefore reasonable regulation of cytokine expression facilitates the treatment of pulmonary fibrosis.

The polypeptide designed according to the present disclosure has three targets, and has effects of an MMP inhibitor and inhibition of angiogenesis and integrin. The MMP inhibitor starts with regulating the ECM and the key cytokines MMP/TIMP in lung injury, an angiogenesis inhibitor can inhibit the release of cytokines such as TGF-β1 and VGFE. As the integrin can bind to TGF-β and promote the activation of TGF-β to release cytokine TGF-β1, inhibiting the integrin can inhibit the release of TGF-β1 and can inhibit the proliferation and activation of fibroblasts, and the inhibitor can act on the treatment of pulmonary fibrosis from the main pathogenesis in pathology.

2. Hepatic Fibrosis

As a pathological change caused by chronic liver damage resulting from a variety of reasons, hepatic fibrosis features excessive and abnormal deposition of extracellular matrix components in the liver, and affects the function of the liver. The hepatic fibrosis is a necessary stage for the development of chronic liver disease to cirrhosis. Factors that can cause almost all kinds of chronic liver diseases can cause hepatic fibrosis, and disease causes may roughly fall into infectious diseases, congenital metabolic defects, chemical toxicities, autoimmune liver diseases, and the like. Excessive deposition of extracellular matrix in the liver is a characteristic change of hepatic fibrosis. At present, it is believed that the activation of hepatic stellate cells (HSCs) is a central link of hepatic fibrosis. However, a mechanism of occurrence and progression of hepatic fibrosis is very complicated. At present, the research mainly focuses on the activation and transformation of hepatic stellate cells into myofibroblasts and fibroblasts. Possible ways are activation of a TGF-β signal transduction pathway, a PDGF receptor-mediated signal transduction pathway, a TNF-α-mediated signal transduction pathway, cyclooxygenase-2 (COX-2), diffuse ECM, angiogenesis, oxidative stress-mediated hepatic fibrosis, or the like.

Hepatic fibrosis is a necessary pathological stage for all kinds of chronic hepatitis to develop into cirrhosis, and is the manifestation of liver injury self-repair. According to a WHO report, there are 20 million cases of hepatitis B virus infection in China, and hepatic fibrosis has occurred to most of these patients. Therefore, how to treat hepatic fibrosis has become an urgent problem to be resolved.

3. Renal Fibrosis

As the common pathway of almost all renal diseases to end-stage renal failure, renal fibrosis (including glomerular fibrosis, renal interstitial fibrosis, and renal vascular fibrosis) is one of the main pathological manifestations of various chronic renal diseases, and is the final outcome of various glomerular, vascular and tubulointerstitial diseases. Studies have shown that no matter what the cause of kidney disease is, the development of renal fibrosis is progressive, and glomerular fibrosis and renal interstitial fibrosis play an important role.

Due to stimulation by various pathogenic factors such as trauma, infection, inflammation, blood circulation disorder, and immune response, intrinsic cells of the kidney are damaged, and deposition and accumulation of a large amount of collagen occur when the disease progresses to a later stage, causing the renal parenchyma to gradually harden and form scars until the kidneys completely loses organ functions. The process of fibrosis and hardening of intrinsic cells in the kidney is also the process of renal fibrosis. In the process of renal fibrosis, the infiltration of renal interstitial inflammatory cells, activation of fibroblasts and excessive deposition of extracellular matrix are all related to the abnormal expression of integrin. The basic pathological cause of renal fibrosis is the excessive activation of fibroblasts. Inhibiting the excessive activation of fibroblasts can effectively inhibit the development of renal fibrosis.

At present, most drugs for treatment of renal fibrosis have problems such as high toxicity, low safety, and single pharmacological effect. Polypeptide drugs have higher drugability than general chemical drugs, have high biological activity, high specificity and relatively weak toxic reaction, and do not easily accumulate in the body. A polypeptide may be designed according to its pathogenesis, is under a multitarget design, and can inhibit the occurrence of renal fibrosis in multiple ways.

4. Skin Fibrosis

Skin fibrosis is excessive scar formation of skin and a result of pathological wound healing response. Skin wound healing includes several stages: hemostasis, inflammation, proliferation, and tissue maturation. The whole process is induced and regulated by a series of complex factors (such as growth factors and cytokines). Skin fibrosis can be driven by immune, autoimmune, and inflammatory mechanisms. The balance between collagen synthesis and degradation plays a key role in the pathological process of fibrosis. Some cytokines, such as TGF-β and interleukin-4 (IL-4), promote wound healing and fibrosis, while other cytokines, such as interferon-γ (IFN-γ) and tumor necrosis factor-α (TNF-α), resist fibrosis. Fibroblasts of normal skin are in a dormant state. After skin injury, fibroblasts begin to activate and massively proliferate, express α-smooth muscle actin (α-SMA), and synthesize a large number of connective tissue proteins.

The most common method used to treat skin fibrosis is immunosuppressive therapy. The basic principle is that autoimmune causes inflammation of diseases and subsequent tissue damage and fibrosis. Commonly used drugs include methotrexate, cyclophosphamide, and cyclosporine. Although some improvements in immunosuppressive therapy have been observed, concerns about the safety of the drugs and the lack of confirmed clinical data and demonstrable efficacy still exist. Therefore, it is necessary to develop an effective pharmaceutical preparation for the treatment of skin fibrosis, fibrotic skin diseases and pathological scar formation of the skin.

5. Myocardial Fibrosis

Myocardial fibrosis is cardiac interstitial remodeling that features excessive proliferation of cardiac interstitial fibroblasts and excessive deposition and abnormal distribution of collagen. Pathologically, myocardial fibrosis mainly features increased collagen deposition, proportion imbalance of different kinds of collagen, and especially increased proportion and disordered arrangement of type I and type III collagen, accompanied by proliferation of myocardial fibroblasts. The synthesis and degradation of extracellular matrix are affected by multiple factors, and the balance between matrix metalloproteinase-9 and tissue inhibitor-1 thereof is a main regulating factor in the degradation process. At present, increasing attention is paid to the role of MMP-9/TIMP-1 in myocardial fibrosis. Myocardial fibrosis is closely related to a variety of cardiovascular diseases, such as hypertension, chronic heart failure, and dilated cardiomyopathy, and is a potential risk factor of sudden cardiac death. At present, the specific pathogenesis of myocardial fibrosis is not very clear. It is mainly believed that myocardial fibrosis is closely related to a renin-angiotensin-aldosterone system, various cytokines, oxidative stress, and the like. These factors affect the occurrence and progression of myocardial fibrosis through the same or different conduction pathways.

At present, no marketed drug for treating myocardial fibrosis is available, and therefore it is necessary to develop a drug for treating myocardial fibrosis.

SUMMARY

1. To-be-Resolved Problem

In view of a situation in which most of existing drugs for treating fibrosis are chemical drugs, and the chemical drugs have problems such as high toxicity, low safety, and single pharmacological actions, the present disclosure provides use of a fused polypeptide with multifunctional activities, which has a good therapeutic effect on lung fibrosis, hepatic fibrosis, renal fibrosis, myocardial fibrosis, skin fibrosis, and lung tissue lesions. The polypeptide according to the present disclosure contains a plurality of domains, can target a plurality of targets, and can inhibit the occurrence of fibrosis in multiple ways.

2. Technical Solutions

To resolve the foregoing problems, technical solutions adopted by the present disclosure are as follows:

A fused polypeptide with multifunctional activities is provided, where the polypeptide comprises the following domains:

```
                                         (SEQ ID NO: 5)
Pro-Arg-Cys-X-Y-Gly-Glu (where X may be Trp or Tyr; and Y may be Arg or
Cys);
and (SEQ ID NO: 6)
Gly-Gly-Gly-Gly-Ile-Val-Arg-Arg-Ala-Asp-Arg-Ala- Ala-Val-Pro-Gly-Gly-Gly-Arg-Gly-Asp.
```

That is, a polypeptide sequence is

```
                                         (SEQ ID NO: 7)
  Pro-Arg-Cys-X-Y-Gly-Glu-Gly-Gly-Gly-Gly-Ile-

Val-Arg-Arg-Ala-Asp-Arg-Ala-Ala-Val-Pro-Gly-

Gly-Gly-Gly-Arg-Gly-Asp.
```

Preferably, an amino acid sequence of the polypeptide is as follows:

```
polypeptide I (SEQ ID NO: 1):
Pro-Arg-Cys-Trp-Arg-Gly-Glu-Gly-Gly-Gly-Gly-Ile- Ala-Val-Val-Arg-Arg-Ala-Asp-Arg-Ala-Pro-Gly-Gly- Gly-Gly-Arg-Gly-Asp;

polypeptide II (SEQ ID NO: 2):
Pro-Arg-Cys-Tyr-Arg-Gly-Glu-Gly-Gly-Gly-Gly-Ile-

Val-Arg-Arg-Ala-Asp-Arg-Ala-Ala-Val-Pro-Gly-Gly-

Gly-Gly-Arg-Gly-Asp;

polypeptide III (SEQ ID NO: 3):
Pro-Arg-Cys-Trp-Cys-Gly-Glu-Gly-Gly-Gly-Gly-Ile- Val-Arg-Arg-Ala-Asp-Arg-Ala-Ala-Val-Pro-Gly-Gly- Gly-Gly-Arg-Gly-Asp;
and polypeptide IV (SEQ ID NO: 4):
Pro-Arg-Cys-Tyr-Cys-Gly-Glu-Gly-Gly-Gly-Gly-Ile- Val-Arg-Arg-Ala-Asp-Arg-Ala-Ala-Val-Pro-Gly-Gly- Gly-Gly-Arg-Gly-Asp;
and
``` use of the fused polypeptide with multifunctional activities in the preparation of anti-pulmonary fibrosis, anti-hepatic fibrosis, anti-renal fibrosis, anti-myocardial fibrosis and anti-skin fibrosis drugs and drugs for resisting lung tissue lesions is provided.

Preferably, the lung tissue lesions include bacterial pneumonia, viral pneumonia, *mycoplasma* pneumonia, fungal pneumonia, *chlamydia* pneumonia, and protozoal pneumonia.

The polypeptide according to the present disclosure has three targets, which target angiogenesis, integrins and matrix metalloproteinases respectively to inhibit the process of fibrosis from three aspects respectively. The polypeptide reduces the activation of fibroblasts and the deposition of extracellular matrix, can slow down the fibrosis process, and can further inhibit the infection of various lung diseases.

3. Beneficial Effects

Compared with the prior art, the present disclosure has the following beneficial effects:

(1) The fused polypeptide with multifunctional activities according to the present disclosure can be used for treating various fibrosis diseases, including pulmonary fibrosis, hepatic fibrosis, renal fibrosis, myocardial fibrosis, and skin fibrosis. Components of the polypeptide are all natural amino acids, which are easy to synthesize, have no obvious toxic or side effects, and have high safety.

(2) In a pulmonary fibrosis model, the polypeptide according to the present disclosure can significantly reduce the expression content of HYP and TGF-β1 in lung tissues, significantly improve a situation of pulmonary fibrosis, and prolong its life cycle.

(3) In a hepatic fibrosis model, the polypeptide according to the present disclosure can significantly reduce the expression content of AST, ALT and HYP in liver tissues, and significantly improve a situation of hepatic fibrosis.

(4) In a renal fibrosis model, the polypeptide according to the present disclosure can significantly reduce the expression content of TGF-β1 in renal tissues and significantly improve a situation of renal fibrosis.

(5) In a myocardial fibrosis model, the polypeptide according to the present disclosure can significantly reduce the content of HYP in heart tissues and significantly improve a situation of myocardial fibrosis.

(6) In a skin fibrosis model, the polypeptide can significantly reduce the expression content of HYP in skin and significantly improve a situation of skin scar hyperplasia.

(7) The polypeptide according to the present disclosure also has a good inhibitory effect on the infection of lung diseases, and the inhibitory rate is 75% or above.

(8) The polypeptide according to the present disclosure is a multi-target drug, and can inhibit the process of fibrosis in multiple ways.

DESCRIPTION OF EMBODIMENTS

Figure 1:
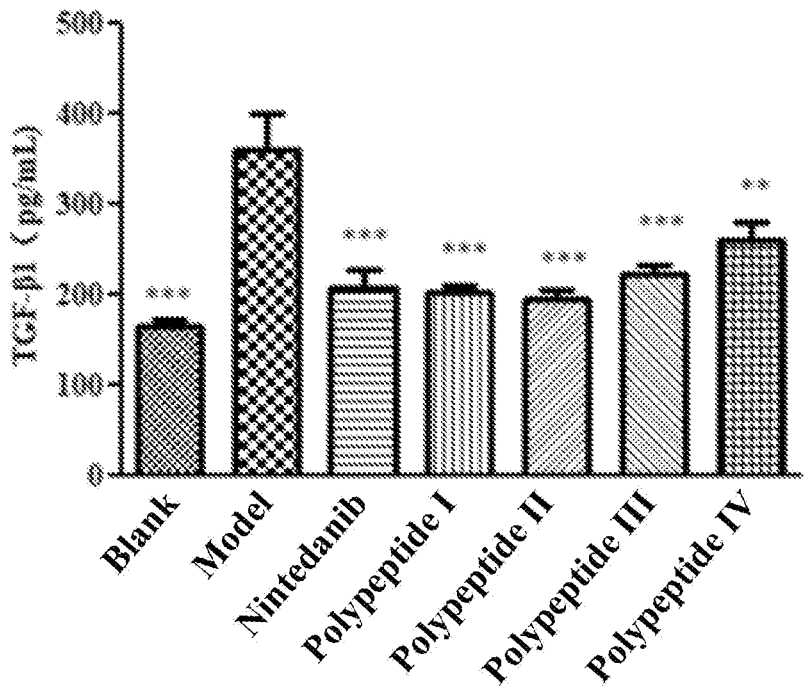
FIG. 1 is a diagram showing that polypeptides I, II, III and IV according to the present disclosure can lower the hydroxyproline content in a pulmonary fibrosis model.

The polypeptide is synthesized by using a conventional solid phase synthesis method.

Embodiment 1 Pulmonary Fibrosis Animal Model

Experimental Animals and Materials:
1. Experimental Animals:
Source and strain: clean SD rats, provided by Comparative Medicine Center of Yangzhou University (laboratory animal production license: SCXK (Su) 2012-0004); Certification of Using of Laboratory Animal: SYXK (Su) 2012-0035).

Weight: 180-200 g at the time of purchase, 190-210 g at the beginning of modeling, and 180-200 g at the beginning of administration.
Gender: Male.
2. Experimental Materials:

| | |
|---|---|
| Bleomycin | Manufacturer: Han Hui Pharmaceutical Co., Ltd. |
| Normal saline | Manufacturer: Anhui Double Crane Pharmaceutical Co., Ltd. |
| Chloral hydrate | Manufacturer: Sinopharm Chemical Reagent Co., Ltd. |
| Rat TGF-β1 ELISA kit | Manufacturer: Tianjin Annuo Ruikang Biotechnology Co., Ltd. |
| Alkaline HYP kit | Manufacturer: Nanjing Jiancheng Bioengineering Institute |
| BIBF1120 (nintedanib) | Manufacturer: Jinan Synovel Chemical Co., Ltd. |

3. Experimental Method:
SD rats were anesthetized by intraperitoneal injection of 1 mL/100 g 4% chloral hydrate. After anesthesia, the rats were fixed and their necks were disinfected by using cotton with 75% alcohol. The skin of the rat neck was longitudinally cut with scissors, and the fascia and muscle were longitudinally bluntly torn with tweezers to expose the trachea. A syringe was inserted into the trachea to inject 5 mg/kg bleomycin, while a blank group was injected with an equal amount of normal saline. Then a rat plate was quickly erected and rotated, the rats' breathing was observed, the neck wound was sterilized after rotation and was sewn, and an amoxicillin anti-inflammatory drug was sprinkled on the suture. After the operation, the rats were put back into a dry and clean cage for resting, waiting was performed for awakening. The rats were awakened after about 1-2 hours, and then fed normally. On the 7$^{th}$ day after modeling, modeling group animals randomly fell into a model group, a Nintedanib positive drug group, polypeptide I, II, III and IV dosage groups, and a normal control group, and the groups were administered separately for an administration cycle of 14 days. Living situations of rats were observed every day and their weights were weighed. After administration for 14 days, the eyeballs were removed and blood was taken, the rats were dissected, and lungs were taken. The content of TGF-β1 in serum and the content of HYP in lung tissues were detected.
4. Experimental Grouping and Dosage Setting

TABLE 1

Experimental grouping and dosage regimen

| Group | Drug | Dosage | Administration mode | Administration frequency | Quantity |
|---|---|---|---|---|---|
| Blank group | Normal saline | 0.5 mL/200 g | Subcutaneous injection | Twice a day | 14 |
| Model group | Normal saline | 0.5 mL/200 g | Subcutaneous injection | Twice a day | 14 |
| Positive drug | Nintedanib | 25 mg/kg | Intragastric administration | Once a day | 14 |
| Test drug (1) | Polypeptide I | 10 mg/kg | Subcutaneous injection | Twice a day | 14 |
| Test drug (2) | Polypeptide II | 10 mg/kg | Subcutaneous injection | Twice a day | 14 |

TABLE 1-continued

Experimental grouping and dosage regimen

| Group | Drug | Dosage | Administration mode | Administration frequency | Quantity |
|---|---|---|---|---|---|
| Test drug (3) | Polypeptide III | 10 mg/kg | Subcutaneous injection | Twice a day | 14 |
| Test drug (4) | Polypeptide IV | 10 mg/kg | Subcutaneous injection | Twice a day | 14 |

5. Experimental Results (1) Impact of a Polypeptide on the Survival Rate of SD Rats Induced by Bleomycin As shown in Table 2, compared with the survival rate (57.1%) of SD rats in the model group, the survival rate of SD rats in each test drug group was higher than that of the model group, each test drug could significantly increase the survival rate of SD rats, and the survival rate of the polypeptide I group and the survival rate of the polypeptide III group was equivalent to that of the positive drug group. The survival rate of polypeptide IV (92.9%) was higher than that of the positive drug group (85.7%)

TABLE 2

Impact of a polypeptide on survival rate (%) of SD rate with bleomycin-induced pulmonary fibrosis

| Group | Dosage (mg/kg) | Number of animals at the beginning | Number of animals at the end | Survival rate (%) |
|---|---|---|---|---|
| Blank group | — | 14 | 14 | 100 |
| Model group | — | 14 | 8 | 57.1 |
| Positive drug group | 10 | 14 | 12 | 85.7 |
| Polypeptide I | 10 | 14 | 12 | 85.7 |
| Polypeptide II | 10 | 14 | 11 | 78.6 |
| Polypeptide III | 10 | 14 | 12 | 85.7 |
| Polypeptide IV | 10 | 14 | 13 | 92.9 |

(2) Impact of a Polypeptide on the Content of TGF-β1 in Serum of SD Rats with Bleomycin-Induced Pulmonary Fibrosis TGF-β1 is the most important fibrogenic factor. In pulmonary fibrosis, the expression content of TGF-β1 was significantly increased. The result is shown in FIG. 1, and there was a highly significant difference between the model group and the blank group (* $P<0.001$). After administration, all groups could significantly reduce the content of TGF-β1 in serum, the nintedanib positive drug group, the polypeptide I group, the polypeptide II group and the polypeptide III group were highly significantly different from the model group (* $P<0.001$), and the polypeptide IV group was highly significantly different from the model group (** $P<0.01$).

Figure 2:
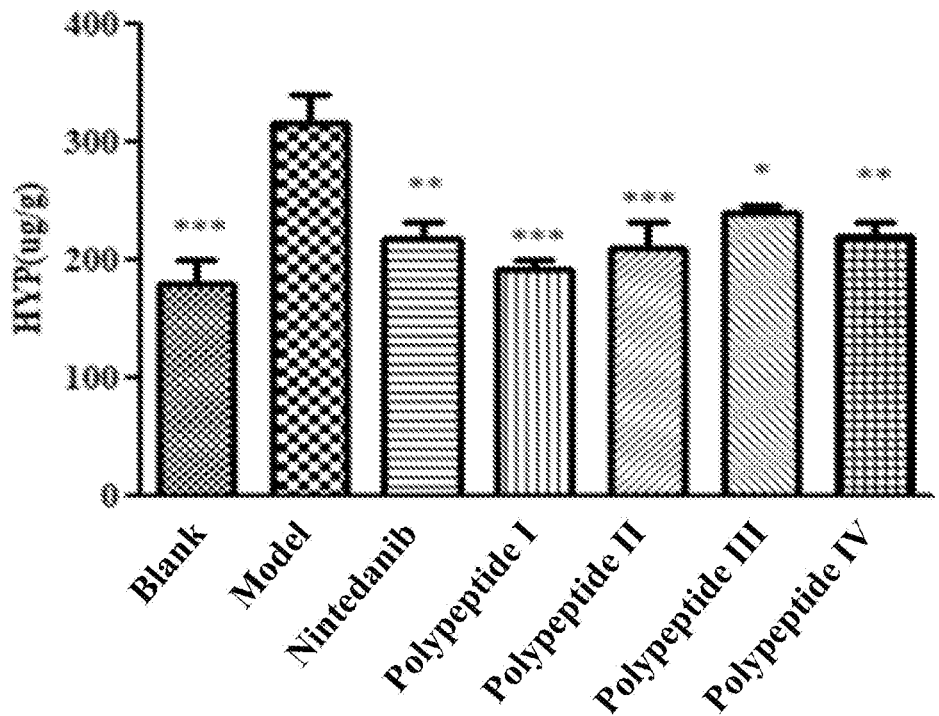
FIG. 2 is a diagram showing that polypeptides I, II, III and IV according to the present disclosure can lower the TGF-β1 content in the pulmonary fibrosis model.

(3) Impact of a Polypeptide on the Content of HYP in SD Rat Lung Tissues with Bleomycin-Induced Pulmonary Fibrosis Lung tissues of each group were taken to detect the content of hydroxyproline in the lung tissue. As the characteristic protein of collagen, hydroxyproline can reflect the content of collagen in the lung tissue from the side. As shown in FIG. 2, the content of HYP in the model group significantly increased, and compared with the blank group, the model group was extremely significantly different (* $P<0.001$). After administration, each group could significantly reduce the expression of HYP in lung tissues. Polypeptide I and polypeptide II could significantly reduce the expression content of HYP in lung tissues, and had better effects than the positive drug, and the polypeptide I group and the polypeptide II group were highly significantly different from the model group (* $P<0.001$). The positive drug group and the polypeptide IV group were highly significantly different from the model group (** $P<0.01$); and the polypeptide III group was significantly different from the model group (* $P<0.05$).

Embodiment 2 Hepatic Fibrosis Animal Model

1. Experimental Animals:

Source and strain: SPF level, SD rats, provided by Shanghai Xipuer-Bikai laboratory Animal Co., Ltd. (laboratory animal license: SCXK (hu) 2013-0016)

Weight: 180-200 g at the time of purchase and 200-220 g at the beginning of modeling Gender: Male.

2. Experimental Materials:

| | |
|---|---|
| Carbon tetrachloride | Manufacturer: Shanghai Aladdin Reagent Co., Ltd. |
| Normal saline | Manufacturer: Anhui Double Crane Pharmaceutical Co., Ltd. |
| Olive oil | Manufacturer: Sangon Biotech (Shanghai) Co., Ltd. |
| Alkaline HYP kit | Manufacturer: Nanjing Jiancheng Bioengineering Institute |
| Glutamic-oxalacetic transaminease test kit | Manufacturer: Nanjing Jiancheng Bioengineering Institute |
| Glutamic-pyruvic transaminase test kit | Manufacturer: Nanjing Jiancheng Bioengineering Institute |

3. Experimental Method

Male SD rats fell into the following groups, and the groups were shown in the following table. There were 10 rats in each group. Modeling was performed on the rats. Each group other than the blank group was injected with 40% CCl₄ intraperitoneally twice a week, the first injection was performed at 3 mL/kg, and then administration was performed at 2 mL/kg. Administration was performed for 8 weeks, and a total of 16 injections were provided to induce hepatic fibrosis. After the intraperitoneal injection of CCl₄ for the fourth time, polypeptide therapy was started on the next day, and administration was performed by subcutaneous injection once a day until the end of induction. After the intraperitoneal injection of CCl₄ for the fourth time, colchicine was administrated on the next day at 200 μg/kg, 5 times a week, and intragastric administration therapy was implemented. After induction for 8 weeks, the administration was stopped. On the second day, the SD rats were dissected, blood was taken, and the liver tissue was taken and stored in a refrigerator at −80° C. for later use. The expressions of AST and ALT in serum and HYP in the rat liver tissue were detected.

4. Experimental Grouping and Dosage Regimen

TABLE 3

Experimental grouping and dosage regimen

| Group | Drug | Dosage | Administration mode | Administration frequency | Quantity |
|---|---|---|---|---|---|
| Blank group | Normal saline | 0.5 mL/200 g | Subcutaneous injection | Once a day | 10 |
| Model group | Normal saline | 0.5 mL/200 g | Subcutaneous injection | Once a day | 10 |
| Positive drug | Colchicine | 0.4 mg/kg | Intragastric administration | 5 times/week | 10 |
| Test drug (1) | Polypeptide I | 6 mg/kg | Subcutaneous injection | Once a day | 10 |
| Test drug (2) | Polypeptide II | 6 mg/kg | Subcutaneous injection | Once a day | 10 |
| Test drug (3) | Polypeptide III | 6 mg/kg | Subcutaneous injection | Once a day | 10 |
| Test drug (4) | Polypeptide IV | 6 mg/kg | Subcutaneous injection | Once a day | 10 |

Figure 3:
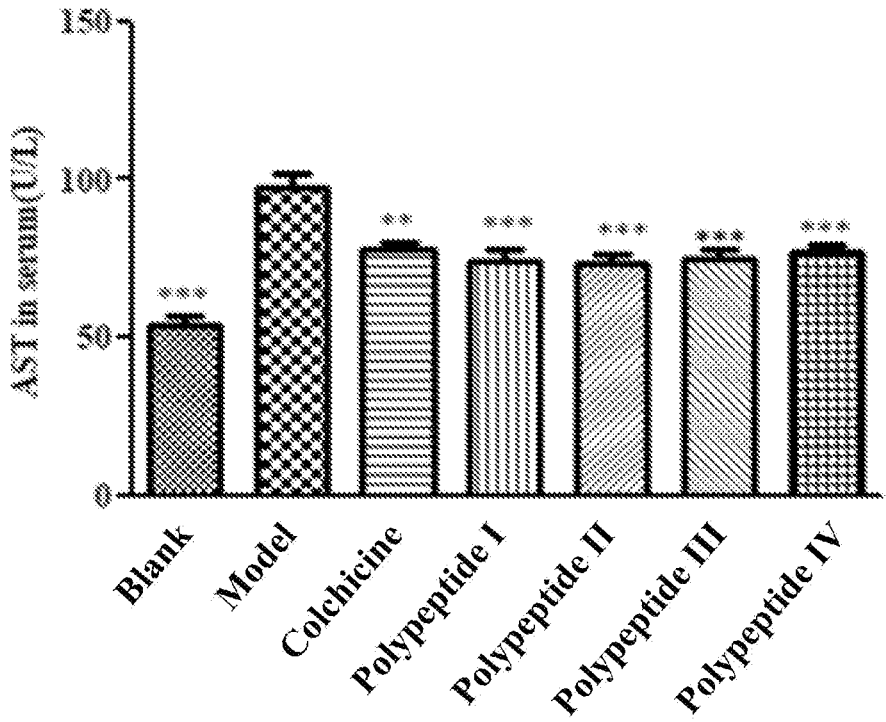
FIG. 3 is a diagram showing that polypeptides I, II, III and IV according to the present disclosure can lower the AST content in a hepatic fibrosis model.
Figure 4:
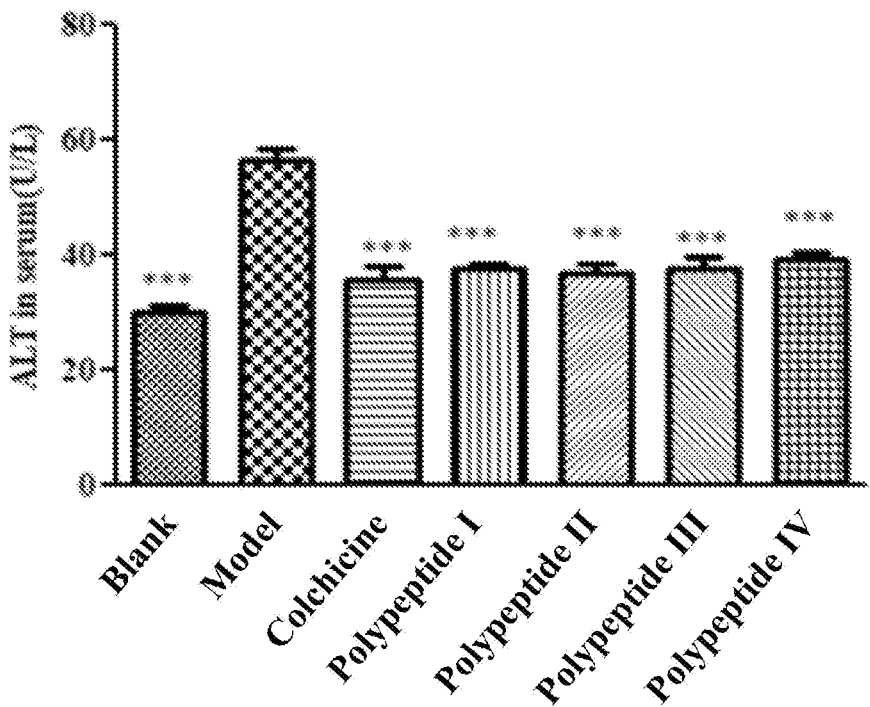
FIG. 4 is a diagram showing that polypeptides I, II, III and IV according to the present disclosure can lower the ALT content in the hepatic fibrosis model.

5. Experimental Results (1) Expressions of AST and ALT in Serum of Rats in Each Group Long-term stimulation with $CCl_4$ could cause liver cell necrosis, inflammation and fibrous tissue proliferation in rats, accompanied by the increase of serum aspartate transaminase (AST) and alanine aminotransferase (ALT), and infiltration of a large number of inflammatory cells and deposition of a large number of collagen in extracellular matrix occurred. The contents of AST and ALT in the serum of rats in the normal group, the colchicine group and each polypeptide group were significantly lower than those in the model group, the levels of ALT and AST in serum in the model group were significantly higher than those in the normal group, and the model group was highly significantly different from the normal group (* $P<0.001$). The content of AST in serum in the colchicine group could be lowered, and the colchicine group was highly significantly different from the model group ( $P<0.01$). Polypeptides I, II, III and IV could reduce the content of AST in serum, and the polypeptide I group, the polypeptide II group, the polypeptide III group and the polypeptide IV group were highly significantly different from the model group (* $P<0.001$). The results are shown in FIG. 3. Each administration group could remarkably lower the content of ALT in serum, and was highly significantly different from the model group (* $P<0.001$). The results are shown in FIG. 4.

(2) Content of HYP in the Liver Tissue of Rats in Each Group

Figure 5:
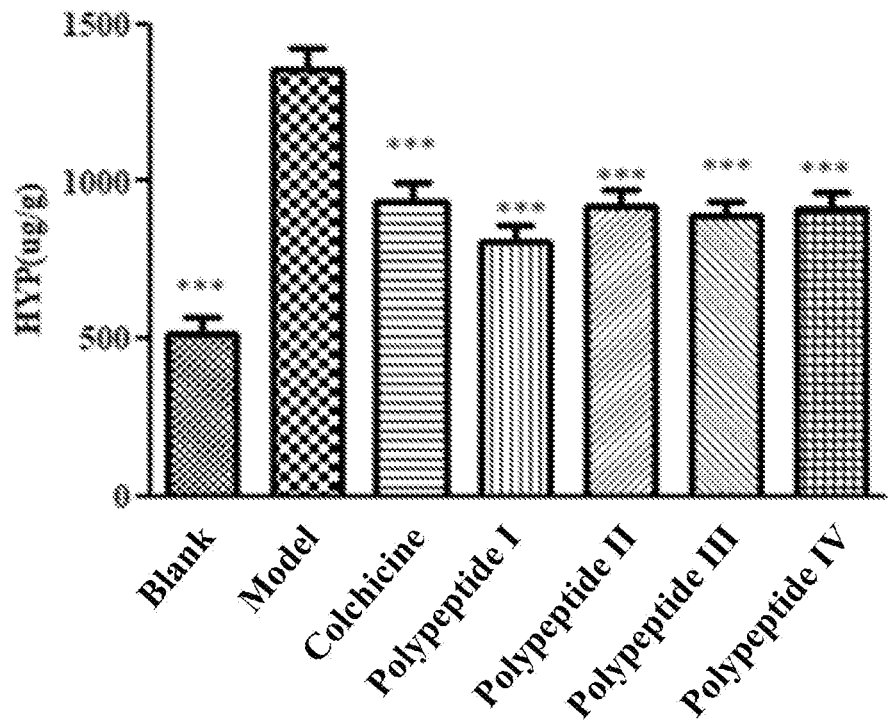
FIG. 5 is a diagram showing that polypeptides I, II, III and IV according to the present disclosure can lower the hydroxyproline content in the hepatic fibrosis model.

Liver tissues of each group were taken to detect the content of hydroxyproline in the liver tissue. As the characteristic protein of collagen, hydroxyproline can reflect the content of collagen in the liver tissue from the side. As shown in FIG. 5, the content of HYP in the model group was significantly higher than that in the blank group. Polypeptides I, II, III and IV and colchicine, the positive drug, could significantly lower the expression of HYP in liver tissue, and each polypeptide group and the positive drug group were highly significantly different from the model group (*** $P<0.001$).

Embodiment 3 Establishment of a Renal Fibrosis Model

1. Experimental Animals

Clean grade male SD rats, purchased from Nanjing Qinglong Mountain Animal Farm, and weighed 180-200 g at the time of purchase, 190-210 g at the beginning of modeling, and 180-200 g at the beginning of administration.

2. Experimental Materials:

| Normal saline | Manufacturer: Anhui Double Crane Pharmaceutical Co., Ltd. |
| Rat TGF-β1 ELISA kit | Manufacturer: Tianjin Annuo Ruikang Biotechnology Co., Ltd. |
| Alkaline HYP kit | Manufacturer: Nanjing Jiancheng Bioengineering Institute |

3. Experimental Method

A renal fibrosis animal model was established. SD rats were anesthetized with 4% chloral hydrate, injected with 1 mL/100 g intraperitoneally, fixed to an operation board, and sterilized in an operation area for later use. The abdominal cavity was cut open about 3-4 mm to the left of the ventrimeson, left kidney ureter was separated in an operation group, the ureter was ligated and separated close to the ureter near the lower pole of the inferior pole of kidney, and the ureter was cut short between two ligations after the double ligations. Muscular layers and abdominal walls were sewed layer by layer, the suture was disinfected with alcohol. After SD rats woke up, the rats were put into a cage for feeding. In the blank group, ureter was not ligated, and other steps were the same.

Then, the animals fell into a blank group, a model group, and polypeptide administration groups, with 10 animals in each group, and the administration was started on the second day after the operation, and was performed for 14 days. After administration for 14 days, blood was taken and supernatant was taken to detect the content of TGF-β1 in serum.

4. Experimental Grouping and Dosage Setting

TABLE 4

Experimental grouping and dosage regimen

| Group | Drug | Dosage | Administration mode | Administration frequency | Quantity |
|---|---|---|---|---|---|
| Blank group | Normal saline | 0.5 mL/200 g | Subcutaneous injection | Once a day | 10 |
| Model group | Normal saline | 0.5 mL/200 g | Subcutaneous injection | Once a day | 10 |
| Test drug (1) | Polypeptide I | 6 mg/kg | Subcutaneous injection | Twice a day | 10 |
| Test drug (2) | Polypeptide II | 6 mg/kg | Subcutaneous injection | Twice a day | 10 |
| Test drug (3) | Polypeptide III | 6 mg/kg | Subcutaneous injection | Twice a day | 10 |
| Test drug (4) | Polypeptide IV | 6 mg/kg | Subcutaneous injection | Twice a day | 10 |

Figure 6:
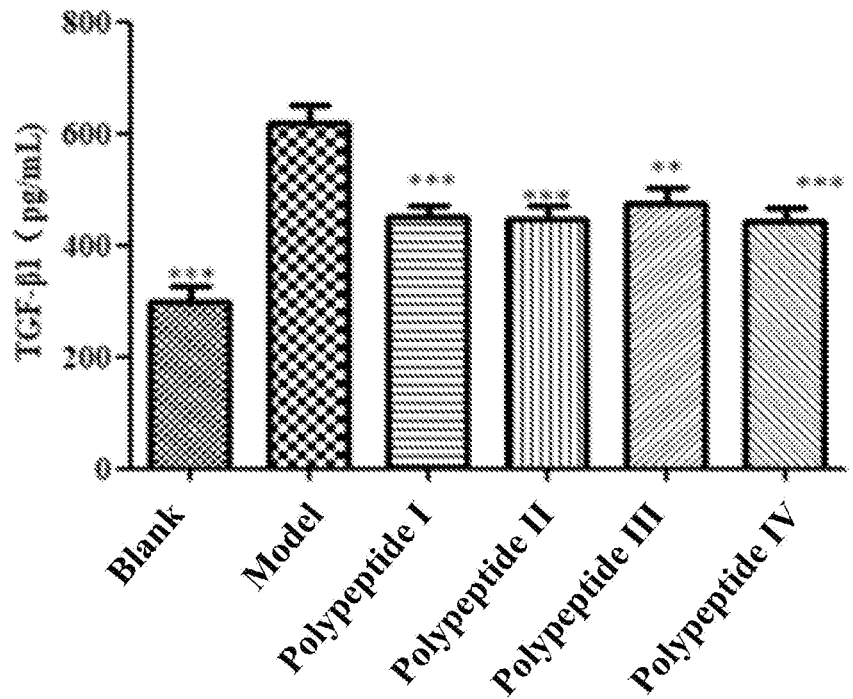
FIG. 6 is a diagram showing that polypeptides I, II, III and IV according to the present disclosure can lower the TGF-β1 content in a renal fibrosis model.

5. Experimental Results (1) Impact of a Polypeptide on the Content of TGF-β1 in Serum of SD Rats with Renal Fibrosis TGF-β1 is the most important fibrogenic factor. In renal fibrosis, the expression of TGF-β1 was significantly increased. The result is shown in FIG. 6, and there was a highly significant difference between the model group and the blank group (* P<0.001). After administration, each group could significantly reduce the content of TGF-β1 in serum, and the polypeptide I group, the polypeptide II group and the polypeptide IV group were highly significantly different from the model group (* P<0.001), and the polypeptide III group was highly significantly different from the model group (** P<0.01).

Embodiment 4 Establishment of a Myocardial Fibrosis Model

1. Experimental Mice: 10-Week-Old Male BALB/c Mice (with an Average Weight of 20 g).
2. Experimental Materials:

| Normal saline | Manufacturer: Anhui Double Crane Pharmaceutical Co., Ltd. |
| Rat TGF-β1 ELISA kit | Manufacturer: Tianjin Ammo Riukang Biotechnology Co., Ltd. |
| Isoprenaline (ISO) | Manufacturer: Sigma |

3. Experimental Method

In the model group, the experimental mice were injected with isoprenaline (ISO) (5 mg/kg) subcutaneously on the back of the mice every day for 7 consecutive days, and the mice were injected with normal saline subcutaneously (200 µL/mouse) every day. In the blank group, normal saline was injected subcutaneously (200 µL/mouse) every day. While a model was made, polypeptide drugs were administrated for treatment by subcutaneous injection. After the 8$^{th}$ day, blood was taken and was centrifuged, the supernatant was taken, and the content of TGF-β1 in serum was detected.

4. Experimental Grouping and Dosage Setting

TABLE 5

Experimental grouping and dosage regimen

| Group | Drug | Dosage | Administration mode | Administration frequency | Quantity |
|---|---|---|---|---|---|
| Blank group | Normal saline | 0.2 mL | Subcutaneous injection | Once a day | 10 |
| Model group | Normal saline | 0.2 mL | Subcutaneous injection | Once a day | 10 |
| Test drug (1) | Polypeptide I | 12 mg/kg | Subcutaneous injection | Twice a day | 10 |
| Test drug (2) | Polypeptide II | 12 mg/kg | Subcutaneous injection | Twice a day | 10 |
| Test drug (3) | Polypeptide III | 12 mg/kg | Subcutaneous injection | Twice a day | 10 |
| Test drug (4) | Polypeptide IV | 12 mg/kg | Subcutaneous injection | Twice a day | 10 |

Figure 7:
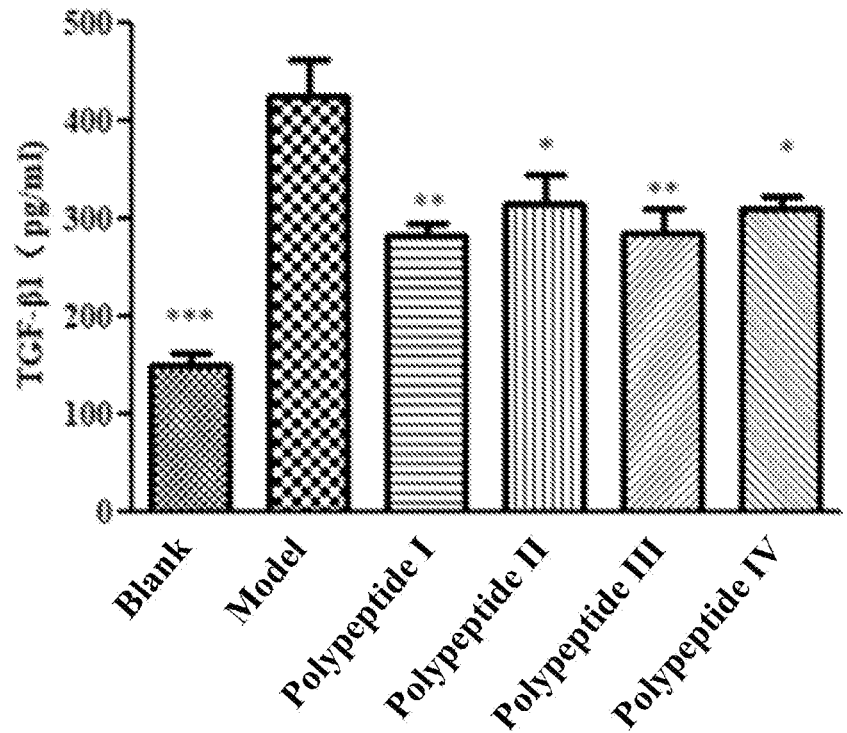
FIG. 7 is a diagram showing that polypeptides I, II, III and IV according to the present disclosure can lower the TGF-β1 content in a myocardial fibrosis model.

5. Experimental Results (1) Impact of a polypeptide on the content of TGF-β1 in serum of mice with myocardial fibrosis TGF-β1 is the most important fibrogenic factor. In myocardial fibrosis, the expression of TGF-β1 was significantly increased. The result is shown in FIG. 7, and there was a highly significant difference between the model group and the blank group (* P<0.001). After administration, each group could significantly reduce the content of TGF-β1 in serum, and the polypeptide I group and the polypeptide III group were highly significantly different from the model group ( P<0.01), and the polypeptide II group and the polypeptide IV group where highly significantly different from the model group (*P<0.05).

Embodiment 5 Establishment of a Skin Fibrosis Model

1. Experimental Animals

Male C57/BL black mice aged 6-8 weeks, purchased from Nanjing Qinglong Mountain Animal Farm.

2. Experimental Materials

| | |
|---|---|
| Bleomycin | Manufacturer: Han Hui Pharmaceutical Co., Ltd. |
| Normal saline | Manufacturer: Anhui Double Crane Pharmaceutical Co., Ltd. |
| Rat TGF-β1 ELISA kit | Manufacturer: Tianjin Annuo Ruikang Biotechnology Co., Ltd. |
| Alkaline HYP kit | Manufacturer: Nanjing Jiancheng Bioengineering Institute |

3. Modeling Method

Bleomycin (10 μg/mL) was injected subcutaneously every day for 28 days to form skin fibrosis. During the modeling period, the administration groups were given polypeptide drugs twice a day for treatment. After modeling, the mice were killed on the next day, and the skin tissue of the mouse back was taken to detect the content of HYP in the skin tissue.

4. Experimental Grouping and Dosage Regimen

TABLE 6

| | Experimental grouping and dosage regimen | | | |
|---|---|---|---|---|
| Group | Drug | Dosage | Administration mode | Administration frequency |
| Blank group | Normal saline | 0.2 mL | Subcutaneous injection | Twice a day |
| Model group | Normal saline | 0.2 mL | Subcutaneous injection | Twice a day |
| Test drug (1) | Polypeptide I | 10 mg/kg | Subcutaneous injection | Twice a day |
| Test drug (2) | Polypeptide II | 10 mg/kg | Subcutaneous injection | Twice a day |
| Test drug (3) | Polypeptide III | 10 mg/kg | Subcutaneous injection | Twice a day |
| Test drug (4) | Polypeptide IV | 10 mg/kg | Subcutaneous injection | Twice a day |

Figure 8:
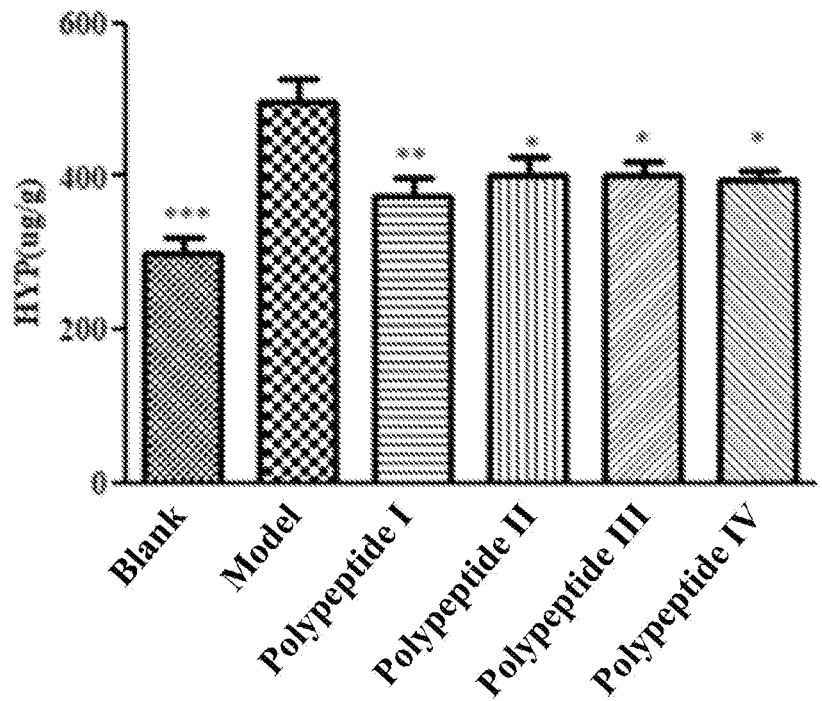
FIG. 8 is a diagram showing that polypeptides I, II, III and IV according to the present disclosure can lower the hydroxyproline content in a skin fibrosis model.

5. Experimental Results (1) Expression of HYP Content in the Skin Tissue of Each Group of Mice The content of hydroxyproline in the skin tissue of the mouse back was detected. As the characteristic protein of collagen, hydroxyproline can reflect the content of collagen in the skin tissue from the side. As shown in FIG. 8, each polypeptide group could reduce the expression of HYP in the skin tissue. Polypeptide I could significantly reduce the expression of HYP in the skin tissue, and the polypeptide I group was highly significantly different from the model group (** $P<0.01$). The polypeptide II group, the polypeptide III group and the polypeptide IV group could reduce the content of HYP in the skin tissue of mice, and were highly significantly different from the model group (*$P<0.05$).

Figure 9:
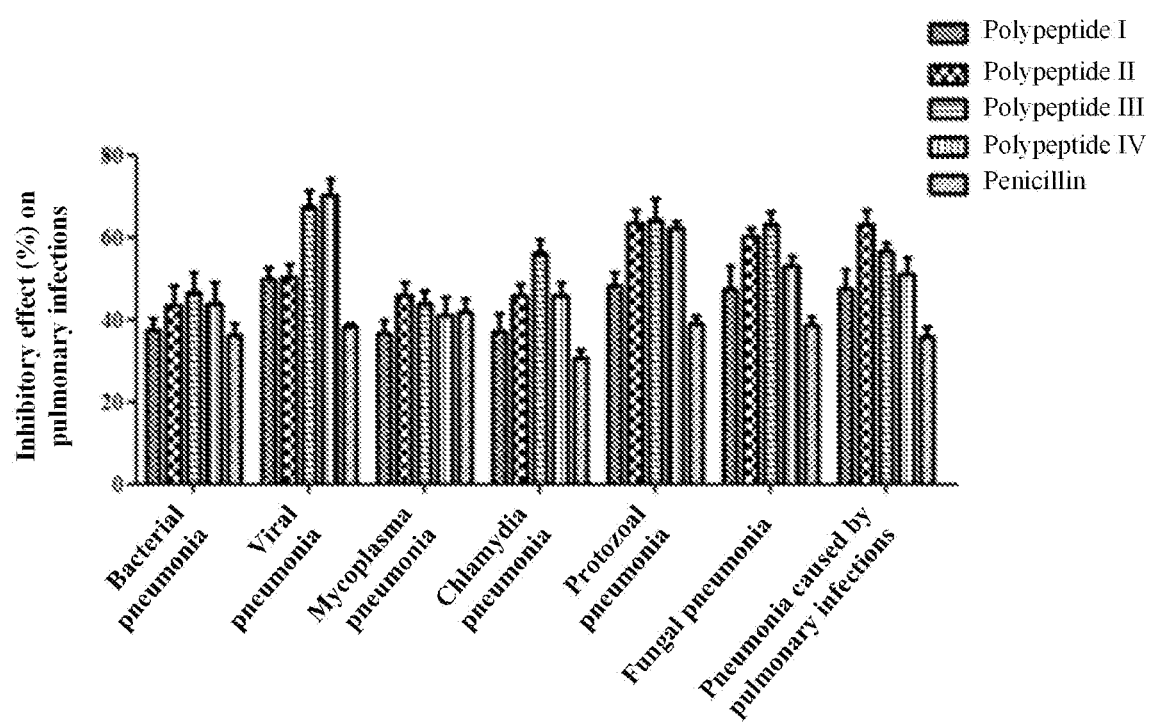
FIG. 9 shows an inhibitory effect of polypeptides I, II, III and IV according to the present disclosure on pulmonary infections.

Embodiment 6 Inhibitory Effect of a Polypeptide According to the Present Disclosure on Multiple Pulmonary Infections A mouse pneumonia model was successfully established by using a nasal drip method. BALB/C mice with a body weight of 18-24 g were selected, and then anesthetized with ether on day 0, day 1 and day 2, respectively, prepared *Streptococcus pneumoniae* bacteria solution, adenovirus concentrated solution, *Mycoplasma pneumoniae*, *Chlamydia pneumoniae*, protozoa and pneumonia fungi were slowly dropped into the nasal cavity of the mice, so that the bacteria solutions entered the trachea and bronchi, and the bacteria solutions were prevented from flowing into the esophagus during the operation to avoid inactivation of the bacteria solutions, so that the mouse pneumonia model was established. After the model was successfully established, the polypeptide according to the present disclosure was administered, as shown in FIG. 9 and Table 7. The results show that compared with the drug in the penicillin administration group, the polypeptide according to the present disclosure had a more significant improvement effect on a plurality of lung infections. The experimental results are represented on the basis of average values+standard deviation.

TABLE 7

Inhibitory effect of a polypeptide according to the
present disclosure on multiple pulmonary infections

| Pneumonia type | Polypeptide I | Polypeptide II | Polypeptide III | Polypeptide IV | Penicillin |
|---|---|---|---|---|---|
| Bacterial pneumonia | 34.83 ± 7.95 | 41.25 ± 9.48 | 47.29 ± 8.76 | 43.69 ± 8.66 | 37.05 ± 4.35 |
| Viral pneumonia | 50.00 ± 6.84 | 50.27 ± 8.08 | 67.49 ± 9.94 | 70.33 ± 9.27 | 48.07 ± 2.07 |
| Mycoplasma pneumonia | 36.48 ± 5.55 | 45.69 ± 5.72 | 43.93 ± 5.53 | 41.20 ± 7.30 | 39.78 ± 5.23 |
| Chlamydia pneumonia | 37.18 ± 7.46 | 45.81 ± 5.21 | 56.40 ± 5.49 | 45.86 ± 5.22 | 32.57 ± 3.13 |
| Protozoal pneumonia | 48.16 ± 5.46 | 63.60 ± 6.16 | 64.29 ± 8.70 | 62.16 ± 3.28 | 40.34 ± 3.02 |
| Fungal pneumonia | 47.54 ± 9.68 | 60.32 ± 3.07 | 62.88 ± 5.94 | 53.22 ± 4.14 | 36.87 ± 2.82 |
| Pneumonia caused by pulmonary infections | 47.52 ± 7.88 | 63.15 ± 5.87 | 56.81 ± 3.13 | 50.99 ± 6.88 | 39.56 ± 4.35 |

What is claimed is:

1. A fused polypeptide with multifunctional activities comprising one of amino acid sequences:

```
polypeptide I (SEQ ID NO: 1):
Pro-Arg-Cys-Trp-Arg-Gly-Glu-Gly-Gly-Gly-Gly-Ile- Val-Arg-Arg-Ala-Asp-Arg-Ala-Ala-Val-Pro-Gly-Gly- Gly-Gly-Arg-Gly-Asp;

polypeptide II (SEQ ID NO: 2):
Pro-Arg-Cys-Tyr-Arg-Gly-Glu-Gly-Gly-Gly-Gly-Ile-

Val-Arg-Arg-Ala-Asp-Arg-Ala-Ala-Val-Pro-Gly-Gly-

Gly-Gly-Arg-Gly-Asp;

polypeptide III (SEQ ID NO: 3):
Pro-Arg-Cys-Trp-Cys-Gly-Glu-Gly-Gly-Gly-Gly-Ile- Val-Arg-Arg-Ala-Asp-Arg-Ala-Ala-Val-Pro-Gly-Gly- Gly-Gly-Arg-Gly-Asp;
and polypeptide IV (SEQ ID NO: 4):
Pro-Arg-Cys-Tyr-Cys-Gly-Glu-Gly-Gly-Gly-Gly-Ile- Val-Arg-Arg-Ala-Asp-Arg-Ala-Ala-Val-Pro-Gly-Gly- Gly-Gly-Arg-Gly-Asp.
```

2. A method for treating fibrosis diseases, characterized by administering to a subject a therapeutically effective amount of a fused polypeptide according to claim 1.

3. A method for treating lung tissue lesions, characterized by administering to a subject a therapeutically effective amount of a fused polypeptide according to claim 1.

4. The method according to claim 2, wherein the fibrosis diseases comprise pulmonary fibrosis, hepatic fibrosis, renal fibrosis, myocardial fibrosis, or skin fibrosis.

5. The method according to claim 3, wherein the lung tissue lesions comprise bacterial pneumonia, viral pneumonia, *mycoplasma* pneumonia, fungal pneumonia, *chlamydia* pneumonia, and protozoal pneumonia.

6. The method according to claim 2, wherein the fused polypeptide is a polypeptide or a pharmaceutically acceptable salt thereof, and a dosage form of the polypeptide or the pharmaceutically acceptable salt thereof is an injection, a capsule, a tablet, a nasal spray or an aerosol.

7. The method according to claim 3, wherein the fused polypeptide is a polypeptide or a pharmaceutically acceptable salt thereof, and a dosage form of the polypeptide or the pharmaceutically acceptable salt thereof is an injection, a capsule, a tablet, a nasal spray or an aerosol.

* * * * *

SEQUENCE LISTING

<160> NUMBER OF SEQ ID NOS: 7

<210> SEQ ID NO 1
<211> LENGTH: 29
<212> TYPE: PRT
<213> ORGANISM: Artificial Sequence
<220> FEATURE:
<223> OTHER INFORMATION: Synthetic

<400> SEQUENCE: 1

Pro Arg Cys Trp Arg Gly Glu Gly Gly Gly Ile Val Arg Arg Ala
1               5                   10                  15

Asp Arg Ala Ala Val Pro Gly Gly Gly Arg Gly Asp
            20                  25

<210> SEQ ID NO 2
<211> LENGTH: 29
<212> TYPE: PRT
<213> ORGANISM: Artificial Sequence
<220> FEATURE:
<223> OTHER INFORMATION: Synthetic

<400> SEQUENCE: 2

Pro Arg Cys Tyr Arg Gly Glu Gly Gly Gly Ile Val Arg Arg Ala
1               5                   10                  15

Asp Arg Ala Ala Val Pro Gly Gly Gly Arg Gly Asp
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic

<400> SEQUENCE: 3

Pro Arg Cys Trp Cys Gly Glu Gly Gly Gly Ile Val Arg Arg Ala
1               5                   10                  15

Asp Arg Ala Ala Val Pro Gly Gly Gly Arg Gly Asp
            20                  25

```
<210> SEQ ID NO 4
<211> LENGTH: 29
<212> TYPE: PRT
<213> ORGANISM: Artificial Sequence
<220> FEATURE:
<223> OTHER INFORMATION: Synthetic

<400> SEQUENCE: 4

Pro Arg Cys Tyr Cys Gly Glu Gly Gly Gly Gly Ile Val Arg Arg Ala
1               5                   10                  15

Asp Arg Ala Ala Val Pro Gly Gly Gly Gly Arg Gly Asp
            20                  25

<210> SEQ ID NO 5
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: UNSURE
<222> LOCATION: (4)..(4)
<223> OTHER INFORMATION: Xaa is Trp or Tyr
<220> FEATURE:
<221> NAME/KEY: UNSURE
<222> LOCATION: (5)..(5)
<223> OTHER INFORMATION: Xaa is Arg or Cys

<400> SEQUENCE: 5

Pro Arg Cys Xaa Xaa Gly Glu
1               5

<210> SEQ ID NO 6
<211> LENGTH: 22
<212> TYPE: PRT
<213> ORGANISM: Artificial Sequence
<220> FEATURE:
<223> OTHER INFORMATION: Synthetic

<400> SEQUENCE: 6

Gly Gly Gly Gly Ile Val Arg Arg Ala Asp Arg Ala Ala Val Pro Gly
1               5                   10                  15

Gly Gly Gly Arg Gly Asp
            20

<210> SEQ ID NO 7
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: UNSURE
<222> LOCATION: (4)..(4)
<223> OTHER INFORMATION: Xaa is Trp or Tyr
<220> FEATURE:
<221> NAME/KEY: UNSURE
<222> LOCATION: (5)..(5)
<223> OTHER INFORMATION: Xaa is Arg or Cys

<400> SEQUENCE: 7

Pro Arg Cys Xaa Xaa Gly Glu Gly Gly Gly Gly Ile Val Arg Arg Ala
1               5                   10                  15

Asp Arg Ala Ala Val Pro Gly Gly Gly Gly Arg Gly Asp
            20                  25
```